(12) United States Patent
Liu (10) Patent No.: US 9,901,120 B2
(45) Date of Patent: *Feb. 27, 2018

(54) ELECTRONIC CIGARETTE WITH A BUILT-IN BATTERY ROD

(71) Applicant: KIMREE HI-TECH INC., Tortola (VG)

(72) Inventor: Qiuming Liu, Huizhou (CN)

(73) Assignee: HUIZHOU KIMREE TECHNOLOGY CO., LTD., SHENZHEN BRANCH, Shenzhen, Guangdong Province (CN)

( * ) Notice: Subject to any disclaimer, the term of this patent is extended or adjusted under 35 U.S.C. 154(b) by 565 days.

This patent is subject to a terminal disclaimer.

(21) Appl. No.: 14/412,430

(22) PCT Filed: Apr. 10, 2013

(86) PCT No.: PCT/CN2013/074013
§ 371 (c)(1),
(2) Date: Dec. 31, 2014

(87) PCT Pub. No.: WO2014/166079
PCT Pub. Date: Oct. 16, 2014

(65) Prior Publication Data
US 2015/0189919 A1 Jul. 9, 2015

(51) Int. Cl.
*A24F 13/00* (2006.01)
*A24F 47/00* (2006.01)
(Continued)

(52) U.S. Cl.
CPC ........... *A24F 47/008* (2013.01); *A61M 15/06* (2013.01)

(58) Field of Classification Search
CPC ...... A24F 1/24; A24F 1/28; A24F 1/22; A24F 1/04; A24F 1/06; A24F 1/08; A24F 1/10;
(Continued)

(56) References Cited

U.S. PATENT DOCUMENTS

| 8,528,569 B1 * | 9/2013 | Newton | A61M 15/06 |
| | | | 128/202.21 |
| 9,402,421 B2 * | 8/2016 | Liu | A61M 15/06 |

(Continued)

FOREIGN PATENT DOCUMENTS

| CN | 1284493 C | 11/2006 |
| CN | 202774133 U | 3/2013 |
| WO | 2012/142293 A2 | 10/2012 |

*Primary Examiner* — Alex Efta
(74) *Attorney, Agent, or Firm* — Cheng-Ju Chiang (57) ABSTRACT

The present invention provides an electronic cigarette with a battery rod disposed inside. The electronic cigarette comprises an inhalation rod and a battery rod which are mutually connected to form an integral. A connecting end of the inhalation rod disposes a first connector. A connecting end of the battery rod disposes a second connector. The battery rod stretches into the inhalation rod from the connecting end of the inhalation rod, and is accommodated and fixed in the inhalation rod. The connecting end of the inhalation rod and the connecting end of the battery rod are threadedly connected by using the first connector and the second connector to be screwing connected. The electronic cigarette has a shorter length, the structure is more compact, and the assembly is convenient, and the electronic cigarette has a greater amount of aerosol, facilitating to observe the balance of the e-liquid and being able to reduce or avoid users to inhale in e-liquid.

14 Claims, 10 Drawing Sheets

(51) Int. Cl.
*F22B 1/28* (2006.01)
*A61M 15/06* (2006.01)
*A61M 11/04* (2006.01)

(58) Field of Classification Search
CPC .. A24F 1/12; A24F 13/02; A24F 13/22; A24F 47/002; A24F 47/008; A61M 11/04; A61M 11/041; A61M 11/044; A61M 15/00; A61M 15/06
USPC ......... 131/198.1, 175, 198.2, 187, 183, 330, 131/191, 194, 196, 224
See application file for complete search history.

(56) References Cited

U.S. PATENT DOCUMENTS

| | | | |
|---|---|---|---|
| 9,420,831 B2* | 8/2016 | Liu | A61M 15/06 |
| 2011/0304282 A1* | 12/2011 | Li | A24F 47/008 |
| | | | 315/362 |
| 2013/0180533 A1* | 7/2013 | Kim | A24F 47/008 |
| | | | 131/273 |
| 2013/0192622 A1* | 8/2013 | Tucker | H01C 17/00 |
| | | | 131/329 |
| 2013/0228191 A1* | 9/2013 | Newton | A61M 15/06 |
| | | | 131/329 |

* cited by examiner

ELECTRONIC CIGARETTE WITH A BUILT-IN BATTERY ROD

CROSS REFERENCE TO RELATED APPLICATIONS

The present application is a 35 U.S.C. § 371 National Phase conversion of International (PCT) Patent Application No. PCT/CN2013/074013, filed on Apr. 10, 2013, the disclosure of which is incorporated by reference herein. The PCT International Patent Application was filed and published in Chinese.

FIELD OF THE INVENTION

The present invention relates to electronic cigarettes, especially an electronic cigarette with a built-in battery rod.

BACKGROUND OF THE INVENTION

Conventional electronic cigarette usually includes an inhalation rod and a battery rod. In the inhalation rod disposes an e-liquid cup for storing e-liquid and an atomizer used to vaporize e-liquid to aerosol. The inhalation rod is usually made of opaque material. Because the battery rod is disposed at one end of the inhalation rod, makes the length of the whole electronic cigarette very long, occupying space; moreover, because a housing of the inhalation rod is made of non-transparent material, it is not convenient to observe balance of the e-liquid in the inhalation rod, thus it may occur that phenomenon of the e-liquid being dried out by the atomizer, even produce unpleasant pungent burning smell.

SUMMARY OF THE INVENTION

The objective of the present invention is to provide an electronic cigarette with a built-in battery, therefore the length is shorter, the structure is more compact and the assembly is convenient.

To achieve the aforementioned objective, the present invention provides an electronic cigarette with a built-in battery rod, comprising an inhalation rod and a battery rod which are mutual connected forming an integral; the inhalation rod comprises a cartridge acting as a housing of the inhalation rod, an e-liquid cup disposed in the cartridge for storing e-liquid, an atomizer used to make e-liquid to be vaporized to aerosol and a mouthpiece cover assembly disposed at one end of the cartridge for users sucking. The battery rod comprises a sleeve acting as a housing of the battery rod and a battery disposed in the sleeve operable to supply working power for the inhalation rod. A connecting end of the inhalation rod disposes a first connector. A connecting end of the battery rod disposes a second connector. The battery rod stretches into the inhalation rod from the connecting end of the inhalation rod, and is accommodated and fixed in the inhalation rod. The connecting end of the inhalation rod and the connecting end of the battery rod are threadedly connected and fixed by using the first connector and the second connector.

Furthermore, the cartridge is made of transparent material.

Furthermore, the first connector defines an inner thread hole therein, while on the second connector disposes an outer thread column which is threadedly connected with the inner thread hole.

Furthermore, the first connector comprises a cartridge seat disposed at a bottom of the cartridge for sealing the bottom of the cartridge, a cylindrical liquid-isolating tube passing through the cartridge seat, extending into the cartridge and fixed on the cartridge seat, and a connecting sleeve disposed on an inner sidewall of a bottom of the liquid-isolating tube. In the connecting sleeve defines the inner thread hole; correspondingly, the second connector comprises a sleeve seat disposed at a bottom of the sleeve for sealing the bottom of the sleeve. A top of the sleeve seat is securely connected with the sleeve; the sleeve seat forms an outer thread column formed at a middle thereof and matching with the inner thread hole; the bottom of the sleeve seat disposes a seat body for users taking and holding.

Furthermore, the central of the cartridge seat disposes a mounting hole axially through used to install the liquid-isolating tube; the bottom of the liquid-isolating tube is tensioningly fixed in the mounting hole.

Furthermore, between a seat body of the sleeve seat and the outer thread column further disposes an annual groove for installing a sealing ring.

Furthermore, in the battery rod disposes a control board for controlling the atomizer working; the sleeve seat further defines an accommodating chamber therein; the control board is accommodated in the accommodating chamber.

Furthermore, on a top of the liquid-isolating tube further disposes a first electrode assembly; correspondingly, one end of the battery rod opposite to the connecting end of the battery rod disposes a second electrode assembly for matching with the first electrode assembly; the battery rod inserts into the inhalation rod, making a positive electrode and a negative electrode of the first electrode assembly to respectively abut with a positive electrode and a negative electrode of the second electrode assembly and then conduct the circuit.

Furthermore, the first electrode assembly comprises a first seat body and a first electrode pole acting as the positive electrode and the negative electrode of the atomizer respectively; the first seat body and the liquid-isolating tube are securely connected; the first electrode pole uses a first insulation piece to be inserted and accommodated in the central of the first seat body, and two ends of the first electrode pole exposed; correspondingly, the second electrode assembly comprises a second seat body and a second electrode pole acting as a positive electrode and a negative electrode of the battery respectively; the second seat body and a top of the sleeve are securely connected; the second electrode pole uses a second insulation piece to be inserted and accommodated in the central of the second seat body, and two ends of the second electrode pole exposed.

Furthermore, a space between an inner sidewall of the cartridge and an outer sidewall of the liquid-isolating tube together with a space between the cartridge seat and the mouthpiece cover assembly together limit an enclosed space forming the e-liquid cup for storing e-liquid; the liquid-isolating tube is made of transparent plastic material.

Furthermore, on the second connector defines an inner thread hole, while on the first connector disposes an outer thread column which is thread connected with the inner thread hole.

Furthermore, in the inhalation rod further disposes an atomization seat assembly used to fix the atomizer and for the atomizer working inside; the atomization seat assembly includes an atomization seat and an atomization cover; the atomization seat and the atomization cover are mutually clamped to clamping fix the atomizer, and between the atomization seat and the atomization cover forms an atomization chamber for the atomizer to vaporize e-liquid to aerosol inside thereof.

Furthermore, in the inhalation rod further disposes a sleeve assembly acting as a aerosol channel; the sleeve assembly wraps the atomization seat assembly inside; the sleeve assembly includes a first sleeve and a second sleeve which are mutually sleeved to form a hollow pipe inside thereof to act as aerosol channel; the first sleeve and the second sleeve mutually sleeve to further clamping fix the atomizer.

Furthermore, the atomizer includes a heating wire and a liquid-guiding member for absorbing e-liquid and supporting the heating wire; the heating wire winds on the liquid-guiding member; two ends of the first sleeve is open; on the upper sidewall of the first sleeve disposes a latching slot radially through for the liquid-guiding member passing through; the liquid-guiding member is across on the latching slot and stretches out of the first sleeve; a bottom of the second sleeve is open; the second sleeve is sheathed at the upper outside of the first sleeve; the bottom of the second sleeve abuts on the liquid-guiding member and acts with the first sleeve to further clamp the liquid-guiding member; a top of the second sleeve communicates with the mouthpiece.

Furthermore, the mouthpiece cover assembly includes a cartridge top cover disposed on the cartridge and hermetically connected with the cartridge, and a mouthpiece inserted on the cartridge top cover and communicates with the internal of the cartridge; in the internal of the mouthpiece disposes a cooling chamber and an air vent with a predetermined length communicating with the cooling chamber.

By adopting the aforementioned technical solutions, the present invention has the following benefits: firstly, the battery rod is accommodated in the inhalation rod, making the whole length of the electronic cigarette shorter, and the structure is more compact; secondly, at the bottom of the inhalation rod and the bottom of the battery rod respectively disposes the first connector and the second connector which are mutual thread connected by the inner thread hole and the outer thread column, making the assembly more convenient and fast thereof; additionally, the housing of the inhalation rod and the housing of the e-liquid cup are made of transparent material, facilitating to observe the usage and balance of the e-liquid in the internal of the electronic cigarette, may make the users feeling a greater amount of aerosol when smoking, and feeling more like smoking a real cigarette; finally, on the mouthpiece defines cooling chamber and air vent with a predetermined length, being able to reduce or avoid users to inhale in e-liquid.

Embodiments of the present invention will be further described in detail in the following drawings.

DETAILED DESCRIPTION OF THE INVENTION

Figure 1:
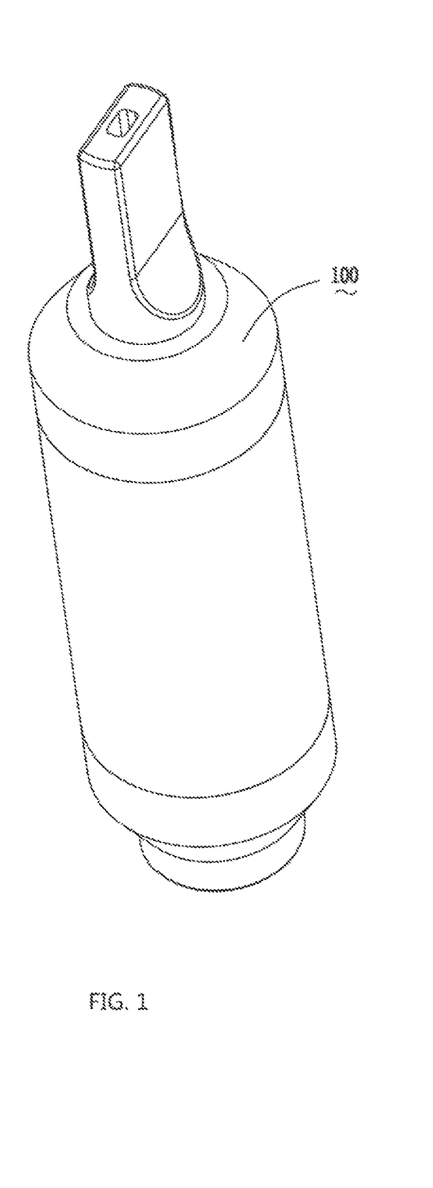
FIG. 1 is a perspective view of an electronic cigarette according to a first embodiment of the present invention.
Figure 2:
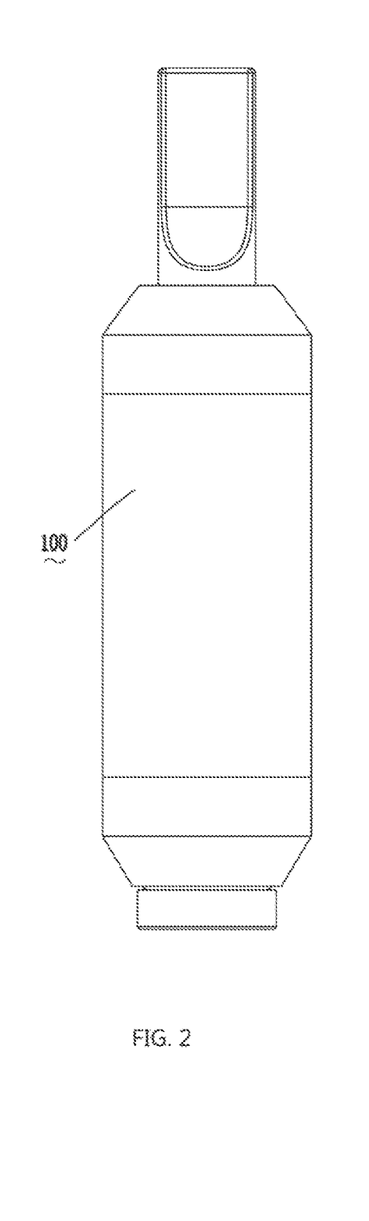
FIG. 2 is a main view of the electronic cigarette according to the first embodiment of the present invention.
Figure 3:
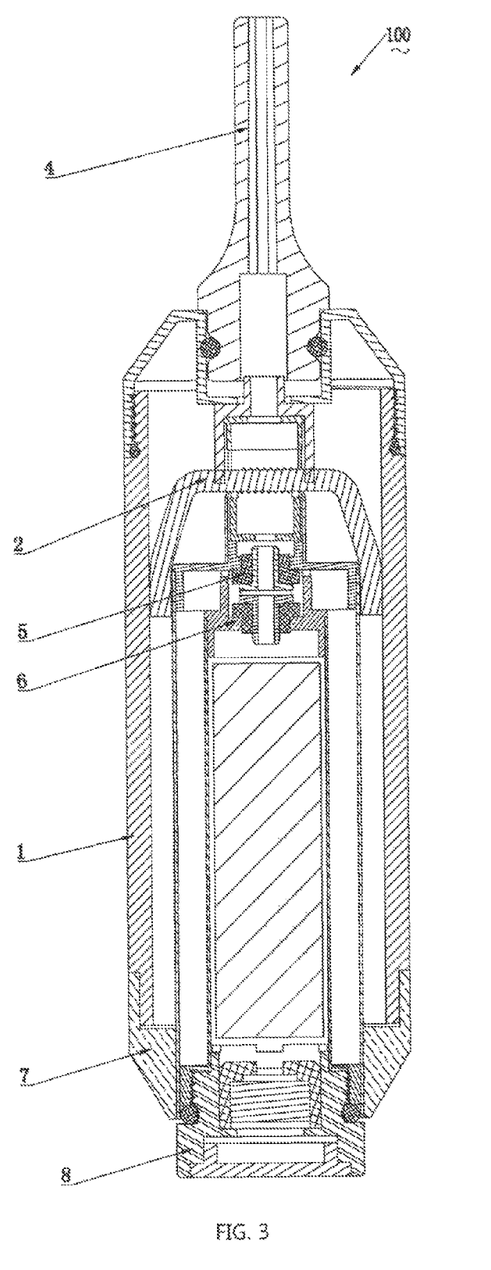
FIG. 3 is a sectional view of the electronic cigarette according to the first embodiment of the present invention.
Figure 4:
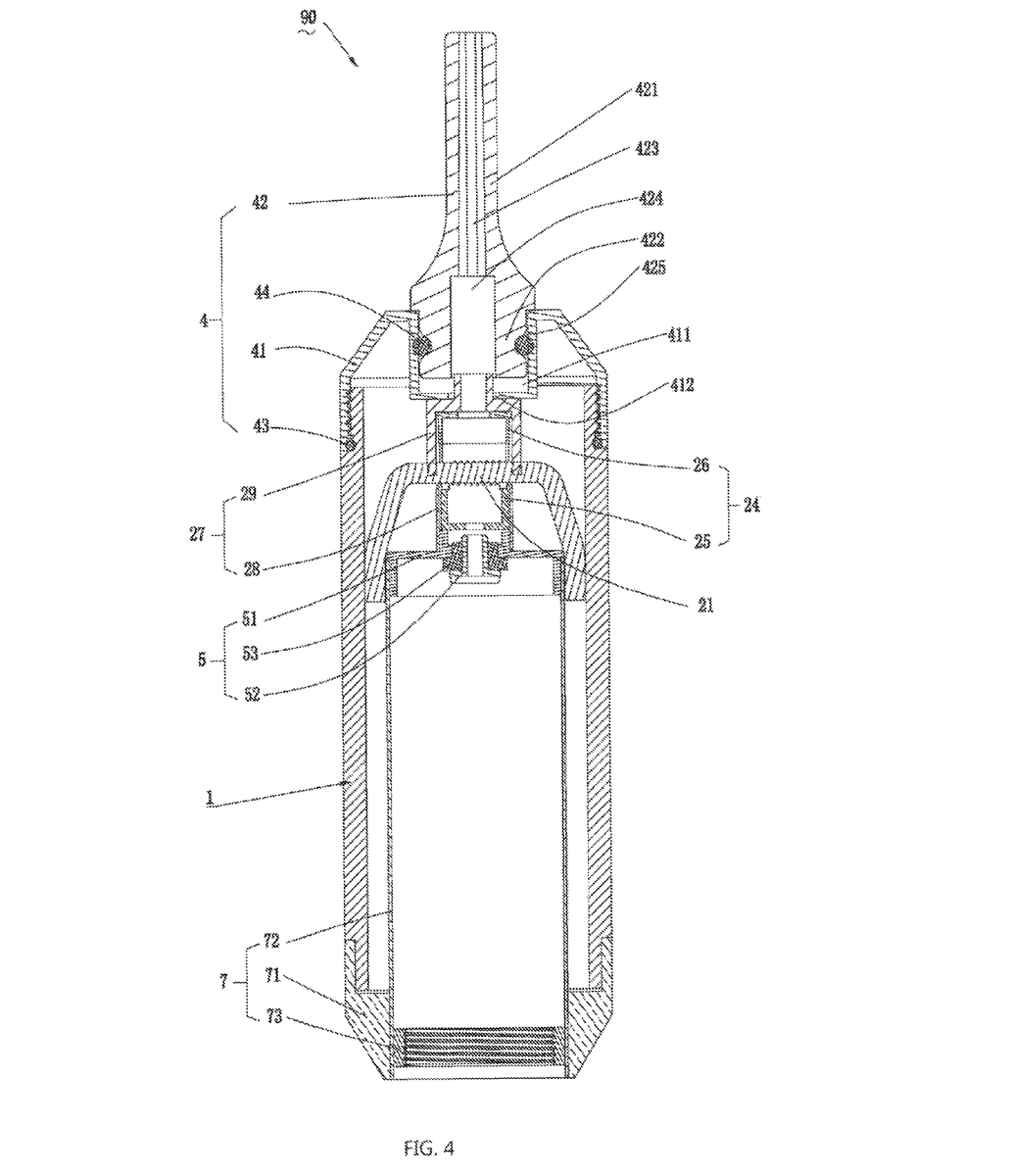
FIG. 4 is a sectional view of an inhalation rod of the electronic cigarette according to the first embodiment of the present invention.
Figure 5:
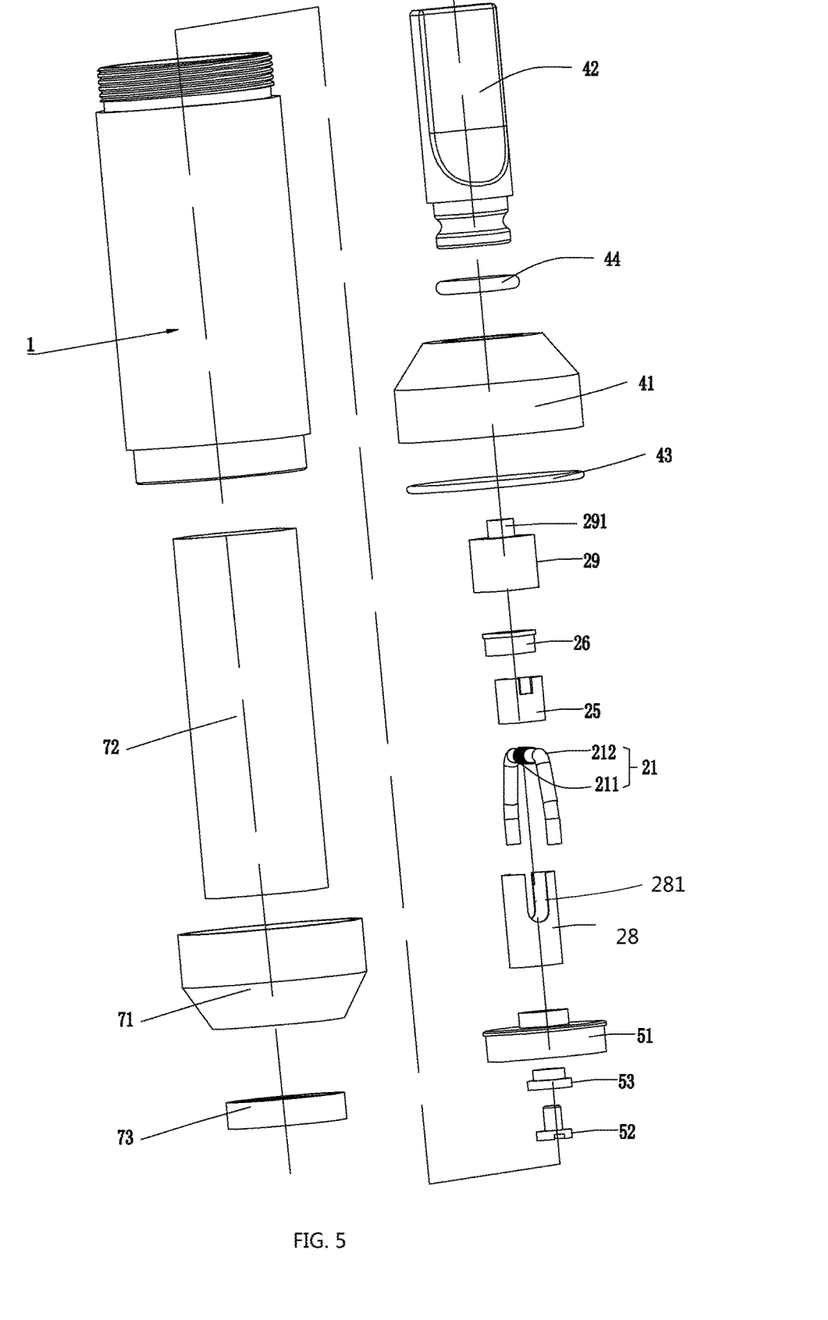
FIG. 5 is an exploded view of the inhalation rod of the electronic cigarette according to the first embodiment of the present invention.
Figure 6:
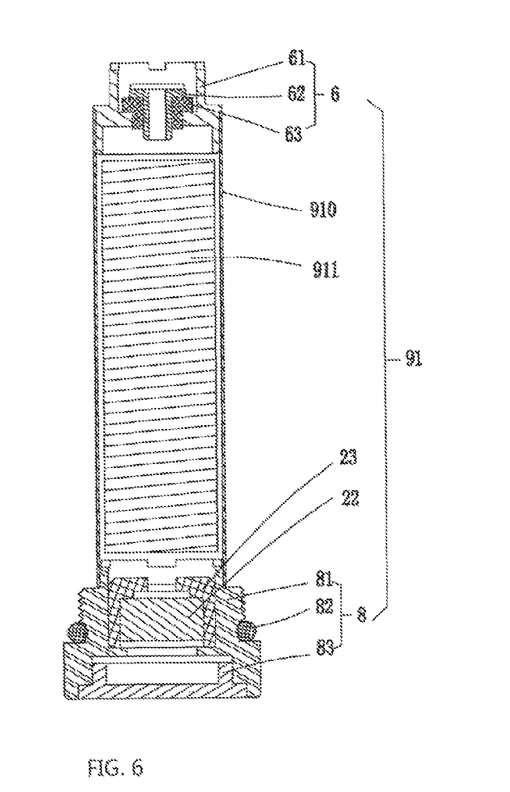
FIG. 6 is a sectional view of a battery rod of the electronic cigarette according to the first embodiment of the present invention.
Figure 7:
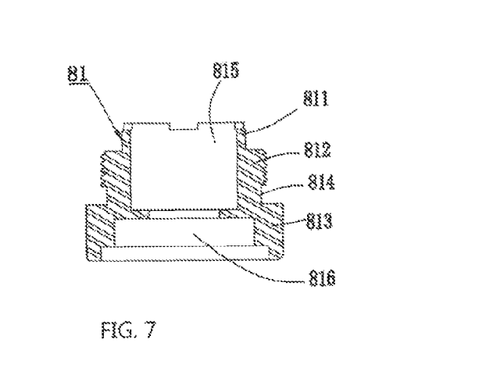
FIG. 7 is a sectional view of a sleeve seat of a battery rod of the electronic cigarette according to a second embodiment of the present invention.
Figure 8:
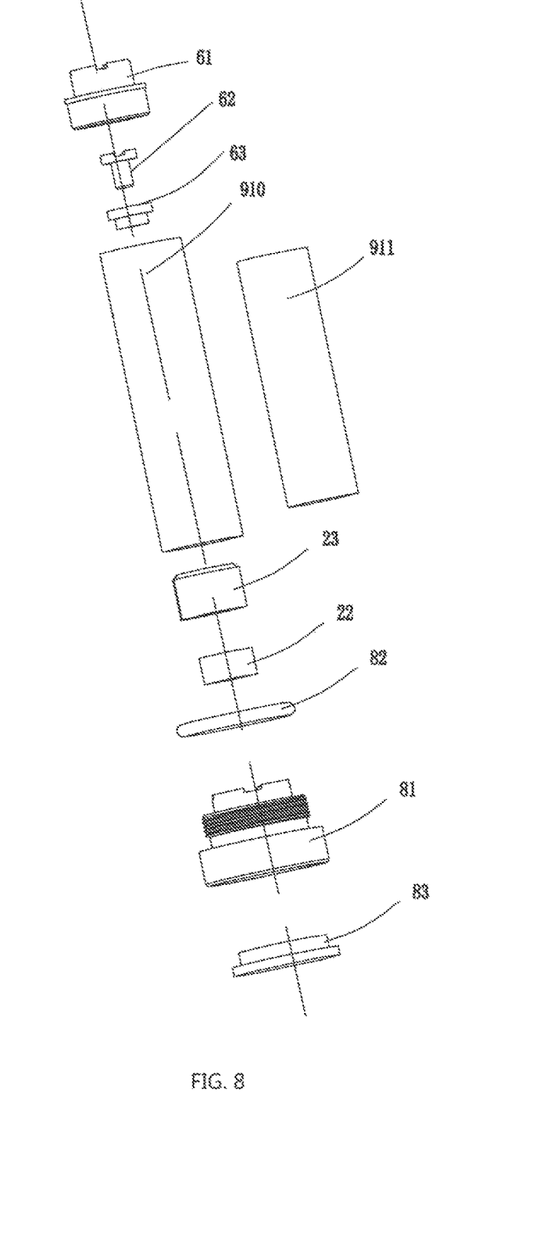
FIG. 8 is an exploded view of the battery rod of the electronic cigarette according to the second embodiment of the present invention.
Figure 9:
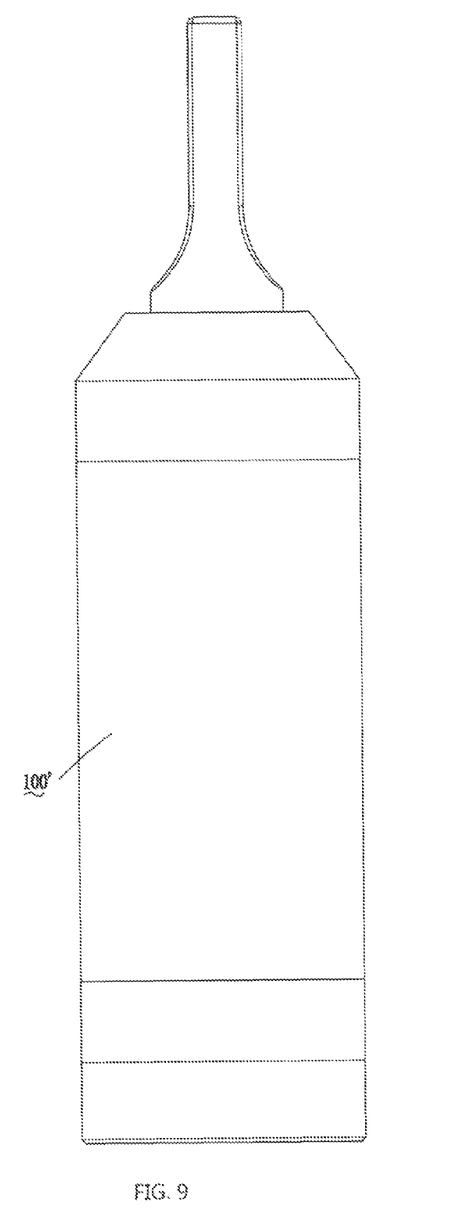
FIG. 9 is a main view of the electronic cigarette according to the second embodiment of the present invention.
Figure 10:
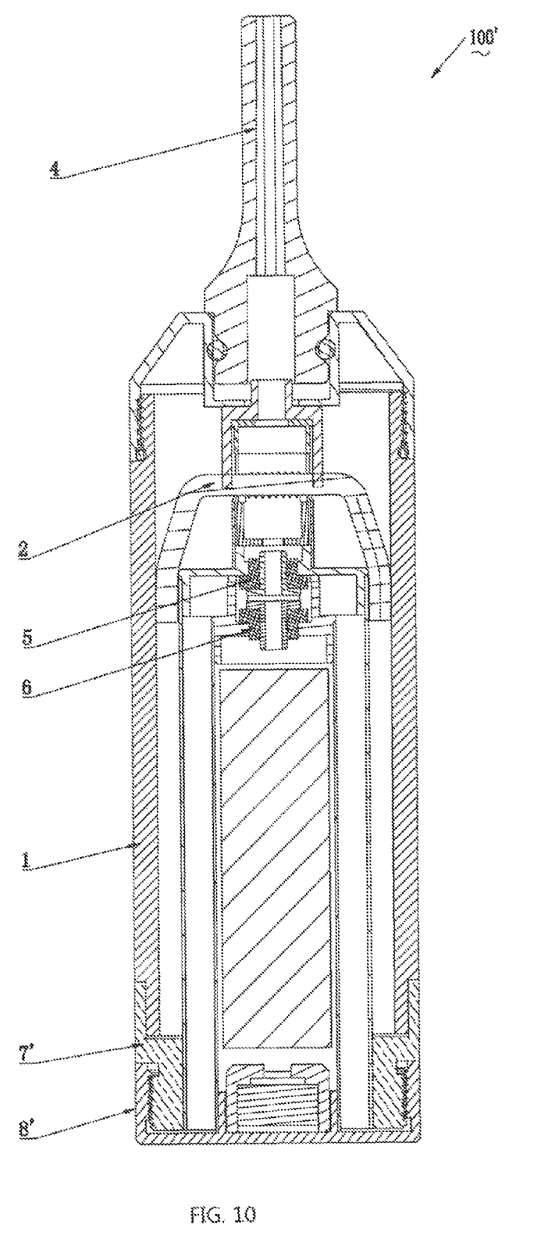
FIG. 10 is a sectional view of the electronic cigarette according to the second embodiment of the present invention.
Figure 11:
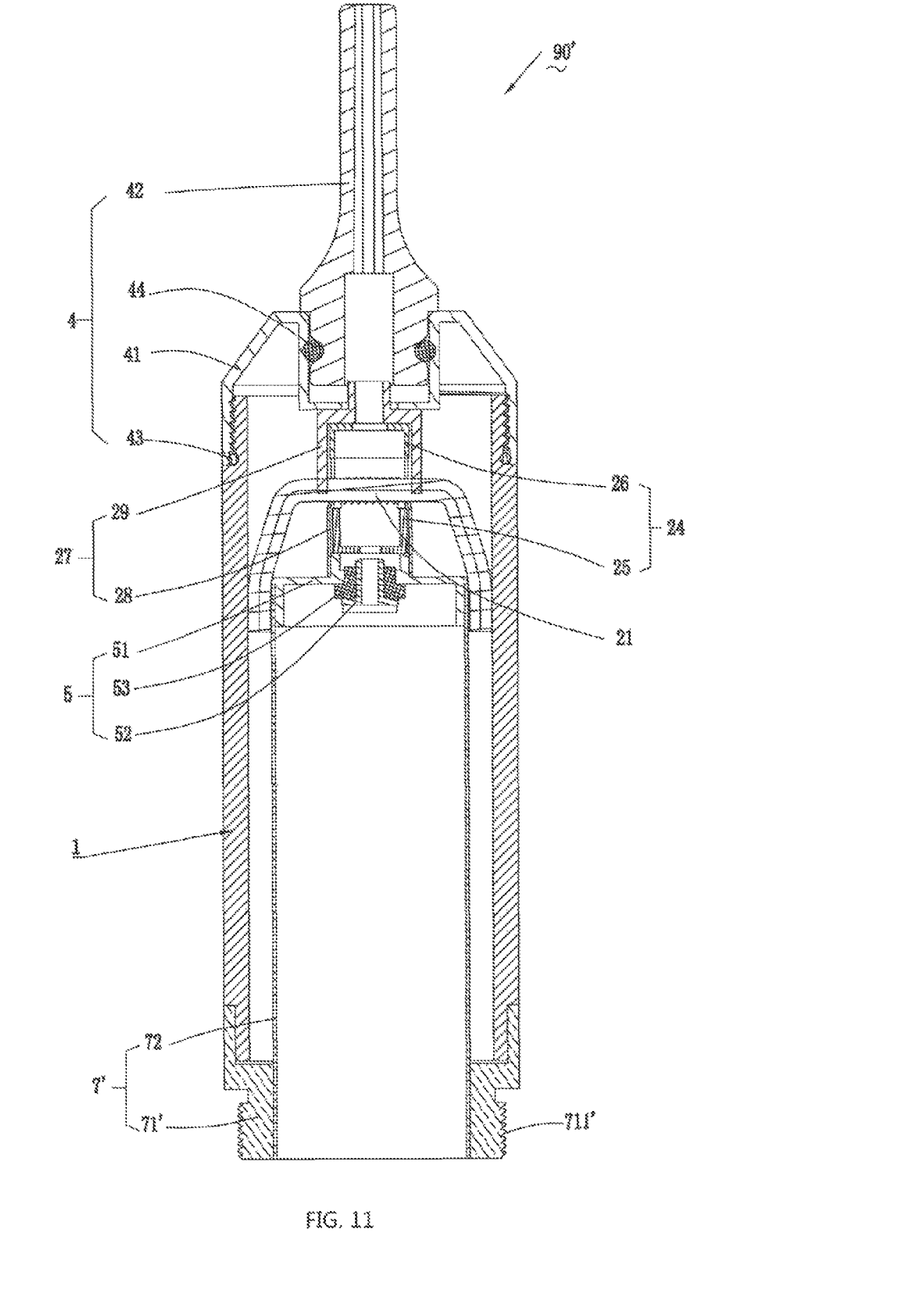
FIG. 11 is a sectional view of the inhalation rod of the electronic cigarette according to the second embodiment of the present invention.
Figure 12:
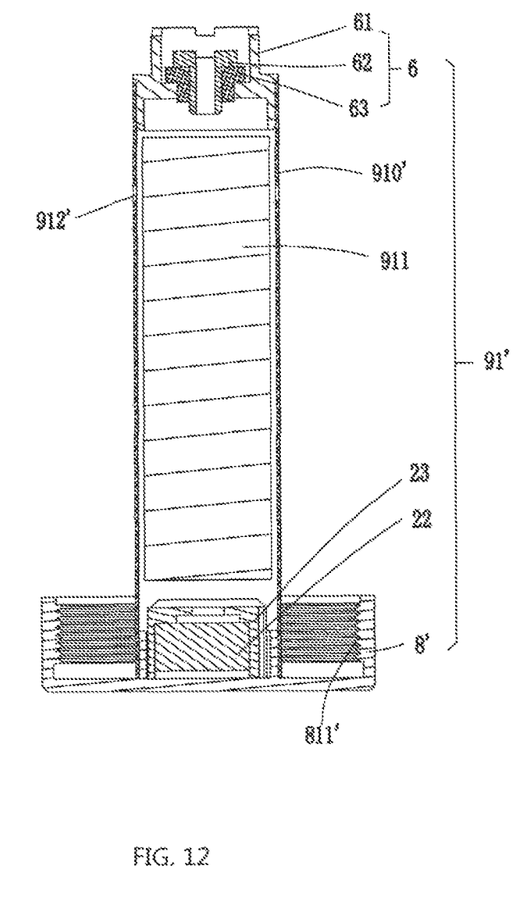
FIG. 12 is a sectional view of the battery rod of the electronic cigarette according to the second embodiment of the present invention.

It is needed to state that embodiments and all element limitations in all embodiments may be combined in the case of no conflicts. The present invention will be described in detail in the following combining figures and embodiments. To facilitate the description, the direction shown in FIG. 1 is as a standard in the embodiment.

Referring to FIG. 1 to FIG. 8, a first embodiment of the present invention provides an electronic cigarette 100. The electronic cigarette 100 includes an inhalation rod 90 and a battery rod 91. The battery rod 91 is inserted and accommodated in the inhalation rod 90. A bottom of the battery rod 91 and a bottom of the inhalation rod 90 are connected by thread so as to make the battery rod 91 and the inhalation rod 90 being connected and fixed.

Referring to FIG. 3 to FIG. 6, the inhalation rod 90 includes a cylindrical cartridge 1 acting as a housing of the inhalation rod 90. The cartridge 1 disposes an atomizer 21 therein operable to vaporize e-liquid to aerosol, a sleeve assembly 27 for aerosol circulation, an e-liquid cup (not labeled) for storing e-liquid and a first electrode assembly 5 used to electrically connect with the battery rod 91. A top of the cartridge 1 is a mouthpiece end for users sucking. A bottom of the inhalation rod 90 is a connecting end used to connect with the battery rod 91. The mouthpiece end and the connecting end of the cartridge 1dispose a mouthpiece cover assembly 4 and a first connector 7 respectively. The battery rod 91 includes a cylindrical sleeve 910 acting as a housing of the battery rod 91. A bottom of the sleeve 910 is a connecting end used to connect with the bottom of the inhalation rod 90. A top and the bottom of the sleeve 910 respectively dispose a second electrode assembly 6 which is electrically connected with the first electrode assembly 5 and a second connector 8 which is securely connected with the first connector 7. In the sleeve 910 further disposes a battery 911, a control board 22 for controlling the atomizer 21 working and a control board support 23 used to fix the control board 22. In order to facilitate observing the usage and balance of the e-liquid in the cartridge 1, and avoiding phenomenon of the e-liquid dryout in the cartridge 1, the cartridge 1 is made of transparent plastic material.

The mouthpiece cover assembly 4 includes a cartridge top cover 41 for covering the top of the cartridge 1, a mouthpiece 42 for users sucking, a sealing ring 43 and a sealing ring 44. The cartridge top cover 41 is covered on the top of the cartridge 1 and securely threaded connects with the cartridge 1. The central of the cartridge top cover 41 is recessed to form an accommodating chamber 411. A bottom wall of the accommodating chamber 411 defines an air vent 412. The mouthpiece 42 inserts into the accommodating chamber 411 of the cartridge top cover 41 and is tensioningly fixed on a sidewall of the accommodating chamber 411. Between the cartridge top cover 41 and the cartridge 1 further disposes the sealing ring 43 to prevent aerosol leaking out from the gap between the cartridge top cover 41 and the cartridge 1. The mouthpiece 42 includes a mouthpiece part 421, and an inserting part 422 which is mutually infixed with the accommodating chamber 411. The mouthpiece part 421 has a predetermined length. The central of the mouthpiece part 421 axially runs through to form an air vent 423 with a predetermined length to facilitate to make tiny e-liquid particles mixed in the aerosol cooling down and being condensed on an inner wall thereof, then reduce or avoid users to inhale in e-liquid. In an internal of the inserting part 422 forms a cooling chamber 424 interconnecting with the air vent 423 to facilitate making the tiny e-liquid particles mixed in the aerosol cooling down and being condensed on the inner wall thereof, then reduce or avoid users to inhale in e-liquid. On an outer sidewall of the inserting part 422 disposes an annular groove 425. Between the mouthpiece 42 and the cartridge top cover 41 further disposes the sealing ring 44 to prevent aerosol leaking out from the gap between the mouthpiece 42 and the cartridge top cover 41. The sealing ring 44 is disposed in the annular groove 425.

The electronic cigarette 100 disposes an atomization device 2 therein. The atomizer 21 is one part of the atomization device 2. The atomization device 2 further includes the control board 22 used to control the atomizer 21 working and the control board support 23. The control board 22 is disposed in the control board support 23. The control board 22 disposes a mini pneumatic switch thereon to control the circuit being conducted, and then make a heating wire 211 starting to work. The atomizer 21 includes the heating wire 211 and a liquid-guiding member 212 for absorbing e-liquid and supporting the heating wire 211. The heating wire 211 winds on the liquid-guiding member 212. The liquid-guiding member 212 is able to absorb and store e-liquid, and may be made of fiberglass or materials capable of absorbing and storing e-liquid such as cotton material. In the embodiment, the liquid-guiding member 212 is fixed on a sleeve assembly 27 to be described in the following. Two ends of the heating wire 211 electrically connect to a positive electrode and a negative electrode of a first electrode assembly 5 respectively. The atomization device 2 further includes an atomization seat assembly 24 used to fix the atomizer 21 and for the heating wire 211 of the atomizer 21 working inside thereof. The atomization seat assembly 24 includes an atomization seat 25 and an atomization cover 26. The atomization seat 25 and the atomization cover 26 are mutually clamped to clamping fix the liquid-guiding member 212, and between the atomization seat 25 and the atomization cover 26 forms an atomization chamber for the heating wire 211 to make the e-liquid in the liquid-guiding member 212 to be vaporized into aerosol inside thereof. The atomization device 2 further includes the sleeve assembly 27 acting as an aerosol channel. The sleeve assembly 27 includes a first sleeve 28 and a second sleeve 29 which are mutually sleeved to form a hollow pipe inside thereof to act as aerosol channel. Two ends of the first sleeve 28 are open. An upper sidewall of the first sleeve 28 defines a latching slot 281 radially therethrough for the liquid-guiding member 212 passing through. The liquid-guiding member 212 is across on the latching slot 281 and extends out of the first sleeve 28. A bottom of the first sleeve 28 is sheathed on the first electrode assembly 5. The atomization seat 25 and the atomization cover 26 are accommodated and supported in the first sleeve 28. A bottom of the second sleeve 29 is open and a top of the second sleeve 29 disposes a top wall. The second sleeve 29 is sheathed at an upper outside of the first sleeve 28. The bottom of the second sleeve 29 abuts on the liquid-guiding member 212 and acts with the first sleeve 28 to further clamp the liquid-guiding member 212. The top wall of the second sleeve 29 axially extends outward to form a vent pipe 291 operable to communicate with the accommodating chamber 411. The vent pipe 291 inserts into the accommodating chamber 411 of the cartridge top cover 41 from the air vent 412 and tensioningly fixed in the air vent 412. The sleeve assembly 27 wraps the atomization seat assembly 24 inside, and the function is to make the vaporized aerosol to be concentrated output thereof. The sleeve assembly 27 communicates with the mouthpiece cover assembly 4 directly, which may make users feeling a greater amount of aerosol when smoking, and feeling more like smoking a real cigarette.

The first electrode assembly 5 includes a first seat body 51 and a first electrode pole 52 respectively acting as a positive electrode and a negative electrode of the inhalation rod 90, and further includes a first insulation piece 53 used to make the first seat body 51 and the first electrode pole 52 being mutually insulated and isolated. The first electrode pole 52 uses the first insulation piece 53 to insert in the central of the first seat body 51 and stretch out of the first seat body 51. A positive electrode and a negative electrode of the heating wire 211 of the atomizer 21 electrically connect with the first seat body 51 and the first electrode pole 52 respectively. Similarly, the second electrode assembly 6 includes a second seat body 61 and a second electrode pole 62 respectively acting as a positive electrode and a negative electrode of the battery rod 91, and further includes a second insulation piece 63 used to make the second seat body 61 and the second electrode pole 62 being mutually insulated and isolated. The second electrode pole 62 uses the second insulation piece 63 to insert in the central of the second seat body 61 and stretch out of the second seat body 61. The second seat body 61 and the second electrode pole 62 electrically connect with a positive electrode and a negative electrode of the battery 911 respectively by the control board 22. Both the central of the first electrode pole 52 and the central of the second electrode pole 62 define an air vent (not labeled) which is axially through. On an upper end of the first seat body 51 further disposes a vent pipe used to be mutually infixed with the first sleeve 28.

The first connector 7 includes a cartridge seat 71 disposed at the bottom of the cartridge 1 for sealing the bottom of the cartridge 1, a liquid-isolating tube 72 disposed in the cartridge 1 and a connecting sleeve 73 disposed at a bottom of the liquid-isolating tube 72. The central of the cartridge seat 71 disposes a mounting hole (not labeled) axially through and used to install and fix the liquid-isolating tube 72. The liquid-isolating tube 72 inserts into the cartridge 1 from the mounting hole. The bottom of the liquid-isolating tube 72 uses an outer sidewall to be tensioningly fixed in the mounting hole of the cartridge 71, while the connecting sleeve 73 is tensioningly fixed on an inner sidewall of the bottom of the liquid-isolating tube 72. On the top of the liquid-isolating tube 72 disposes the first electrode assembly 5. The first seat body 51 of the first electrode assembly 5 tensioningly infixed with the liquid-isolating tube 72 and a connecting portion of the first seat body 51 of the first electrode assembly 5 and the liquid-isolating tube 72 is sealed along circumferential thereof. The central of the connecting sleeve 73 disposes an inner thread hole 731 axially through.

In the embodiment, a space between the inner sidewall of the cartridge 1 and the outer sidewall of the liquid-isolating tube 72 together with a space between the cartridge seat 71 and the mouthpiece cover assembly 4 (specifically as the cartridge top cover 41) mutually form the e-liquid cup for storing e-liquid. The two ends of the liquid-guiding member 212 stretch out from the sleeve assembly 27 and then naturally droop to a bottom of the e-liquid cup to facilitate to absorb the e-liquid in the e-liquid cup.

The second connector 8 includes a sleeve seat 81 disposed at the bottom of a sleeve 910 for sealing the bottom of the sleeve 910, and a sealing ring 82 used for make the first connector 7 and the second connector 8 hermetically connected. The sleeve seat 81 is cylindrical, and a top of the sleeve seat 81 disposes an inserting column 811 used to tensioningly connect and fix with the sleeve seat 81 thereof. The central of the sleeve seat 81 forms an outer thread column 812 used to threadedly connect with the connecting sleeve 73. A bottom of the sleeve seat 81 disposes a seat body 813 for users taking and holding; by using the seat body 813 makes the battery rod 91 screwing mounted in the inhalation rod 90 or dismantle the battery rod 91 out from the inhalation rod 90. Between the seat body 813 and the outer thread column 812 further disposes an annual groove 814 for installing the sealing ring 82. In the embodiment, in order to make the structure of the battery rod 91 more simple and compact, the control board support 23 is sheathed in the sleeve seat 81; correspondingly, the e sleeve seat 81 disposes an accommodating chamber 815 used to accommodate the control board support 23. To facilitate observing the electronic cigarette working conditions, at the bottom of the sleeve 910 further disposes an indicating light cover 83 equipped with a working indicating light (not shown) and an air vent (not shown). The indicating light cover 83 is disposed at the bottom of the sleeve seat 81; correspondingly, at the bottom of the sleeve seat 81 further disposes a light cover hole 816 for accommodating the indicating light cover 82. The light cover hole 816 communicates with the accommodating chamber 815.

When assembling, the battery rod 91 stretches into the liquid-isolating tube 72 from an inner thread hole 731 of the connecting sleeve 73, making the second electrode assembly 6 electrically connecting with the first electrode assembly 5, that is, making the second seat body 61 and the first seat body 51 mutually abutting and power on, and making the second electrode pole 61 abutting with the first electrode pole 51. While the bottom of the battery rod 91 uses the outer thread column 812 on the sleeve seat 81 threadedly connecting with the inner thread hole 731 of the connecting sleeve 73 of the inhalation rod 90 to fix. The assembly and disassembly between the battery rod 91 and the inhalation rod 90 are convenient and fast. When smoking, external air enters from the air vent at the bottom of the indicating light cover 83 on the battery rod 91, then enters into the sleeve 910 through the accommodating chamber 815 in the sleeve seat 81, and then flows out of the inhalation rod 90 individually through the air vent of the second electrode pole 62 and the first electrode pole 52, the aerosol channel of the sleeve assembly 27, the air vent 412 of the cartridge top cover 41, the cooling chamber 424 on the mouthpiece 42 and the air vent 423, thus forming an air channel in the electronic cigarette. The air in the electronic cigarette and the external air flow smoothly. Certainly, external air may also directly enter from the air vent 423 on the mouthpiece 42 through the air vent 412 on the cartridge top cover 41 into the cartridge 1 and then arrive at the inner of the sleeve assembly 27. When the e-liquid in the cartridge 1 is exhausted, dismantle the mouthpiece cover 4 and then may continue to add e-liquid into the cartridge 1.

Referring to FIG. 9 to FIG. 12, a second embodiment of the present invention provides an alternative electronic cigarette 100'. The electronic cigarette 100' includes an inhalation rod 90' and a battery rod 91'. The battery rod 91' is also inserted and accommodated in the inhalation rod 90'. The structures of the inhalation rod 90' and the battery rod 91' are basically the same as the structures of the inhalation rod 90 and the battery rod 91 respectively. The inhalation rod 90' includes a first connector 7' with a structure basically the same as the structure of the first connector 7. The first connector 7' includes a cartridge seat 71' with a structure basically the same to the structure of the cartridge seat 71. On the cartridge seat 71' disposes an outer thread column 711'. The battery rod 91' includes a second connector 8' with a structure basically the same to the structure of the second connector 8. The structures of the second connector 8' and the sleeve seat 81 are basically the same. In the second connector 8' disposes an inner thread hole 811' screwing match with the outer thread column 711'. The inhalation rod 90' and the battery rod 91' are tightly fixed by the screwing of the outer thread column 711' and the inner thread hole 811'. In the second connector 8' further disposes the control board 22 and the control board support 23. At a bottom of the second connector 8' does not dispose with the indicating light cover 83. The battery rod 91' includes a sleeve 910'. To facilitate air entering into the battery rod 91', on the sidewall of the sleeve 910' defines an air vent 912' (shown in FIG. 12). Meanwhile, the connecting portion of the outer thread column 711' and the inner thread hole 811' does not dispose with a sealing ring to facilitate air entering into the sleeve 910' through the gap of the screwing matching part. The other matching parts of the first connector 7' and the second connector 8' make adaptive changes only. Here will not describe in detail.

Embodiments of the present invention is shown and described in the above-mentioned. Various improvement and modifications can be made to the embodiments by those skilled in the art without departing from the true spirit and scope of the disclosure. The scope of the present invention is defined by the appended claims and equivalents thereof.

What is claimed is:

1. An electronic cigarette with a built-in battery rod, comprising an inhalation rod and a battery rod which are mutually connected together; the inhalation rod comprising a cartridge acting as a housing of the inhalation rod, an e-liquid cup disposed in the cartridge for storing e-liquid, an atomizer used to make e-liquid to be vaporized to aerosol and a mouthpiece cover assembly disposed at one end of the cartridge for users to suck on; the battery rod comprising a sleeve acting as a housing of the battery rod and a battery disposed in the sleeve operable to supply working power for the inhalation rod; wherein a connecting end of the inhalation rod disposes a first connector, a connecting end of the battery rod disposes a second connector; the battery rod extends into the inhalation rod from the connecting end of the inhalation rod, and is accommodated and fixed in the inhalation rod;

the connecting end of the inhalation rod and the connecting end of the battery rod are threadedly fixed by using the first connector and the second connector;

the first connector defines an inner thread hole, while on the second connector disposes an outer thread column which is threadedly connected with the inner thread hole;

the first connector comprises a cartridge seat disposed at a bottom of the cartridge for sealing the bottom of the cartridge, a cylindrical liquid-isolating tube passing through the cartridge seat, extending into the cartridge and fixed on the cartridge seat, and a connecting sleeve disposed on an inner sidewall of a bottom of the liquid-isolating tube; in the connecting sleeve defines the inner thread hole; the second connector comprises a sleeve seat disposed at a bottom of the sleeve for sealing the bottom of the sleeve; a top of the sleeve seat is securely connected with the sleeve; the sleeve seat forms the outer thread column formed at a middle thereof and matching with the inner thread hole; the bottom of the sleeve seat disposes a seat body for users to hold.

2. The electronic cigarette as claimed in claim 1, wherein the cartridge is made of transparent material.

3. The electronic cigarette as claimed in claim 1, wherein a central portion of the cartridge seat disposes a mounting hole axially through used to install the liquid-isolating tube; the bottom of the liquid-isolating tube is fixed in the mounting hole.

4. The electronic cigarette as claimed in claim 1, wherein between a seat body of the sleeve seat and the outer thread column further disposes an annual groove for installing a sealing ring.

5. The electronic cigarette as claimed in claim 1, wherein in the battery rod disposes a control board for controlling working of the atomizer; the sleeve seat further defines an accommodating chamber therein; the control board is accommodated in the accommodating chamber.

6. The electronic cigarette as claimed in claim 1, wherein on a top of the liquid-isolating tube further disposes a first electrode assembly; one end of the battery rod opposite to the connecting end of the battery rod disposes a second electrode assembly for matching with the first electrode assembly; the battery rod inserts into the inhalation rod, making a positive electrode and a negative electrode of the first electrode assembly to respectively abut with a positive electrode and a negative electrode of the second electrode assembly and then conduct an electrical circuit.

7. The electronic cigarette as claimed in claim 6, wherein the first electrode assembly comprises a first seat body and a first electrode pole acting as a positive electrode and a negative electrode of the atomizer respectively; the first seat body and the liquid-isolating tube are securely connected; the first electrode pole uses a first insulation piece to be inserted and accommodated in the central of the first seat body, and two ends of the first electrode pole are exposed; the second electrode assembly comprises a second seat body and a second electrode pole acting as a positive electrode and a negative electrode of the battery respectively; the second seat body and a top of the sleeve are securely connected; the second electrode pole uses a second insulation piece to be inserted and accommodated in the central of the second seat body, and two ends of the second electrode pole are exposed.

8. The electronic cigarette as claimed in claim 1, wherein a space between an inner sidewall of the cartridge and an outer sidewall of the liquid-isolating tube together with a space between the cartridge seat and the mouthpiece cover assembly together limit an enclosed space forming the e-liquid cup for storing e-liquid; the liquid-isolating tube is made of transparent plastic material.

9. The electronic cigarette as claimed in claim 1, wherein in the inhalation rod further disposes an atomization seat assembly used to fix the atomizer and for the atomizer working inside the atomization seat assembly; the atomization seat assembly includes an atomization seat and an atomization cover; the atomization seat and the atomization cover are mutually clamped to clamping fix the atomizer, and between the atomization seat and the atomization cover forms an atomization chamber for the atomizer to vaporize e-liquid to aerosol therein.

10. The electronic cigarette as claimed in claim 9, wherein in the inhalation rod further disposes a sleeve assembly acting as an aerosol channel; the sleeve assembly wraps the atomization seat assembly inside; the sleeve assembly includes a first sleeve and a second sleeve which are mutually sleeved to form a hollow pipe inside thereof to act as aerosol channel; the first sleeve and the second sleeve mutually sleeve to further clamping fix the atomizer.

11. The electronic cigarette as claimed in claim 10, wherein the atomizer includes a heating wire and a liquid-guiding member for absorbing e-liquid and supporting the heating wire; the heating wire winds on the liquid-guiding member; two ends of the first sleeve are open; a latching slot is radially disposed through an upper sidewall of the first sleeve for the liquid-guiding member passing through; the liquid-guiding member is across on the latching slot and extends out of the first sleeve; a bottom of the second sleeve is open; the second sleeve is sheathed at the upper outside of the first sleeve; the bottom of the second sleeve abuts on the liquid-guiding member and acts with the first sleeve to further clamp the liquid-guiding member; a top of the second sleeve fluidly communicates with the mouthpiece.

12. An electronic cigarette with a built-in battery rod, comprising an inhalation rod and a battery rod which are mutually connected together; the inhalation rod comprising a cartridge acting as a housing of the inhalation rod, an e-liquid cup disposed in the cartridge for storing e-liquid, an atomizer used to make e-liquid to be vaporized to aerosol and a mouthpiece cover assembly disposed at one end of the cartridge for users to suck on; the battery rod comprising a sleeve acting as a housing of the battery rod and a battery disposed in the sleeve operable to supply working power for the inhalation rod; wherein a connecting end of the inhalation rod disposes a first connector, a connecting end of the battery rod disposes a second connector; the battery rod extends into the inhalation rod from the connecting end of the inhalation rod, and is accommodated and fixed in the inhalation rod; the connecting end of the inhalation rod and the connecting end of the battery rod are threadedly fixed by using the first connector and the second connector;

wherein the mouthpiece cover assembly includes a cartridge top cover disposed on the cartridge and hermetically connected with the cartridge, and a mouthpiece inserted in the cartridge top cover and fluidly communicates with the internal of the cartridge; in the internal of the mouthpiece disposes a cooling chamber and an air vent with a predetermined length fluidly communicating with the cooling chamber.

13. An electronic cigarette with a built-in battery rod, comprising:

an inhalation rod, the inhalation rod comprising a cartridge acting as a housing of the inhalation rod, an e-liquid cup disposed in the cartridge for storing e-liquid, an atomizer used to make e-liquid to be vaporized to aerosol and a mouthpiece cover assembly disposed at one end of the cartridge for users to suck on; and a battery rod being mutually connected with the inhalation rode together, the battery rod comprising a sleeve acting as a housing of the battery rod and a battery disposed in the sleeve operable to supply working power for the inhalation rod;

wherein a connecting end of the inhalation rod disposes a first connector, a connecting end of the battery rod disposes a second connector; the battery rod is accommodated in the inhalation rod from the connecting end of the inhalation rod; the connecting end of the inhalation rod and the connecting end of the battery rod are threadedly connected by using the first connector and the second connector;

the second connector defines an inner thread hole, while the first connector disposes an outer thread column which is thread connected with the inner thread hole;

the first connector comprises a cartridge seat disposed at a bottom of the cartridge for sealing the bottom of the cartridge, a cylindrical liquid-isolating tube passing through the cartridge seat, extending into the cartridge and fixed on the cartridge seat, the second connector comprises a sleeve seat disposed at a bottom of the sleeve for sealing the bottom of the sleeve;

the sleeve seat of the second connector forms the inner thread hole; a bottom of the sleeve seat disposes a seat body for users to hold;

the cartridge seat of the first connector disposes the outer thread column;

the inhalation rod and the battery rod are fixed by screwing the outer thread column in the inner thread hole.

14. The electronic cigarette as claimed in claim 13, wherein the cartridge is made of transparent material.

* * * * *